United States Patent [19]

Müller et al.

[11] 4,131,018
[45] Dec. 26, 1978

[54] ELBOW OR BENT TUBE MANIPULATOR, ESPECIALLY FOR ULTRASONIC TESTING IN NUCLEAR REACTOR INSTALLATION

[75] Inventors: Otto Müller, Spardorf; Georg Gugel, Kalchreuth; Hans Kastl, Neustadt, Waldnaab, all of Germany

[73] Assignee: Kraftwerk Union Aktiengesellschaft, Mülheim (Ruhr), Germany

[21] Appl. No.: 831,111

[22] Filed: Sep. 7, 1977

[30] Foreign Application Priority Data

Sep. 6, 1976 [DE] Fed. Rep. of Germany ....... 2640055

[51] Int. Cl.$^2$ ............................................. G01N 29/04
[52] U.S. Cl. ..................................... 73/432 R; 73/623; 73/637; 176/19 R; 324/220
[58] Field of Search ................. 73/619, 633, 635, 637, 73/638, 623, 432R; 324/220; 176/19 R

[56] References Cited

U.S. PATENT DOCUMENTS

| | | | |
|---|---|---|---|
| 3,786,684 | 1/1974 | Wiers et al. | 324/220 X |
| 3,911,750 | 10/1975 | Prasher | 73/432 R |
| 3,929,007 | 12/1975 | Dent et al. | 73/637 |

Primary Examiner—Richard C. Queisser
Assistant Examiner—John P. Beauchamp
Attorney, Agent, or Firm—Herbert L. Lerner

[57] ABSTRACT

Manipulator assembly for testing the material of a pipe elbow from the inside thereof, the pipe elbow being secured to a pipe union extending from a pressure vessel openable for receiving therein a vertically extending manipulator mast having an arm carrying a manipulator, the manipulator being movable by the arm in vertical direction, rotatably about the axis of the mast and in direction of the longitudinal axis of the arm and transversely thereto, the manipulator includes a multimember vehicle drivable in direction of the pipe-union and pipe-elbow axis, the members of the vehicle being articulatingly connected to one another and having extensible and retractable support legs for supporting the respective vehicular members centered relative to the inner periphery of the pipe elbow, the support legs having roller members at the end thereof for transporting the vehicular members in axial direction of the pipe union and the pipe elbow, the vehicular member located at the head of the multimember vehicle being a test system carrier and being drivable with the vehicle in axial direction of the pipe union and the pipe elbow, the test system carrier having a test system fastened to at least one test arm and mounted so as to be rotatable along predetermined test tracks in circumferential direction of the pipe elbow, drivable radially inwardly and outwardly with the test arm and centerable on the respective center of the pipe elbow, the vehicular members and the test system carrier being mutually engaged by articulating couplings and longitudinally adjustable drive members so that, in an extended readiness position thereof wherein the manipulator is disposed in front of the pipe union, the vehicular members and the test system carrier are oriented in axial direction of the pipe union, are centered on the pipe union center and are rigidly coupled to one another, whereas in a travelling position thereof wherein at least the test system of the manipulator is located within the pipe elbow, the vehicular members and the test system carrier are loosely coupled to one another so that they adapt themselves to the curvature of the pipe elbow as they travel in axial direction thereof.

18 Claims, 7 Drawing Figures

ELBOW OR BENT TUBE MANIPULATOR, ESPECIALLY FOR ULTRASONIC TESTING IN NUCLEAR REACTOR INSTALLATION

The invention relates to a manipulator assembly for testing the material of pipe elbows from the inside thereof and, in particular, for ultrasonic (US) testing of welded seam sections of the joints between reactor coolant pipe unions of a reactor pressure vessel, the primary pipeline elbow thereof and the primary line, as well as for ultrasonic testing of the longitudinal seams of such elbows, those welded seam sections being inaccessible from the outside, the manipulator being supported on the arm of a manipulator mast and, within the opened reactor pressure vessel, being movably adjustable in height (z-direction), being rotatable about the axis of the mast and being movably adjustable in longitudinal and transverse directions (x- and y-directions). A device employing a manipulator for carrying out examinations and in-service inspection tests of the inner surfaces of pressure vessels open at the top thereof have become known heretofore from German Pat. DT-SP No. 2,154,015. A similar device has become known from German published prosecuted application DT-AS 2,325,388, with which also the inner circumference or periphery of the primary coolant line of a reactor pressure vessel can be tested by means of a horizontal arm. Furthermore, a test system carrier, especially for ultrasonic testing in nuclear reactor pressure vessels, has already been proposed heretofore, by means of which complicated spatial curves in the vicinity of the outer edges of the pipe union are scannable beforehand. With none of the hereinaforementioned testing devices is it possible, however, to test pipe elbows from the inside thereof. However, there has been a requirement for some time now for such inner testing, since nuclear reactor installations are often equipped with curved reactor coolant lines and the safety officials or authorities also require testing of the welded seams not only from the outside but also from the inside of such pipe elbows. It is accordingly an object of the invention to provide a manipulator assembly for testing the material of a pipe elbow from the inside thereof, and more particularly, for ultrasonically testing curved lengths of a primary coolant line, inaccessible from the outside, in reactor pressure vessels, by means of which individual test tracks are scannable in a defined and reproducible manner by remote control in accordance with a suitable test program. Such a manipulator is of particular importance because, except for ultrasonic testing prior to start-up of the reactor, the aforementioned lengths of pipeline have a relatively high dosage rate which permits working in the vicinity of the pipe lines only for brief periods, if at all, and in protective clothing. With the foregoing and other objects in view, there is provided, in accordance with the invention, a manipulator assembly for testing the material of a pipe elbow from the inside thereof, the pipe elbow being secured to a pipe union extending from a pressure vessel openable for receiving therein a vertically extending manipulator mast having an arm carrying a manipulator, the manipulator being movable by the arm in vertical direction, rotatably about the axis of the mast and in direction of the longitudinal axis of the arm and transversely thereto. The manipulator includes a multimember vehicle drivable in direction of the pipe-union and pipe-elbow axis, the members of the vehicle being articulatingly connected to one another and having extensible and retractable support legs for supporting the respective vehicular members centered relative to the inner periphery of the pipe elbow, the support legs having roller members at the end thereof for transporting the vehicular members in axial direction of the pipe union and the pipe elbow, the vehicular member located at the head of the multimember vehicle being a test system carrier and being drivable with the vehicle in axial direction of the pipe union and the pipe elbow, the test system carrier having a test system fastened to at least one test arm and mounted so as to be rotatable along predetermined test tracks in circumferential direction of the pipe elbow, drivable radially inwardly and outwardly with the test arm and centerable on the respective center of the pipe elbow, the vehicular members and the test system carrier being mutually engaged by articulating couplings and longitudinally adjustable drive members so that, in an extended readiness position thereof wherein the manipulator is disposed in front of the pipe union, the vehicular members and the test system carrier are oriented in axial direction of the pipe union, are centered on the pipe-union center and are rigidly coupled to one another, whereas in a travelling position thereof wherein at least the test system of the manipulator is located within the pipe elbow, the vehicular members and the test system carrier are loosely coupled to one another so that they adapt themselves to the curvature of the pipe elbow as they travel in axial direction thereof. In a more specific sense, the manipulator is employed especially for ultrasonically testing welded seam sections of the joints between main coolant-line unions of a reactor pressure vessel, the primary pipeline elbow thereof and the primary line, as well as for ultrasonically testing longitudinal seams of such elbows, those welded seam sections being inaccessible from the outside. The advantages attainable with the invention are primarily that also the pipe elbows, i.e., the respective portions of the welded seams, can be tested from the inside by ultrasonic means in a defined and reproducible manner, so that test reports can be prepared which attest to the metallurgical condition of the vital main coolant lines, in the interior thereof. The articulating or flexible connection of the vehicular members to one another and with the test system carrier can be effected by means of universal joints, so that also spatially curved pipeline elbows can be scanned. In many cases, however, the pipelines are curved only in one plane, and in this case it is especially advantageous if, in accordance with another feature of the invention, to provide straps articulatingly connecting the vehicular members and the test system carrier so that the multimember vehicle is capable of effecting a deflection or deviation in a given plane corresponding to the curvature of the pipe elbow whereas in other planes axial to the pipe elbow the multimember vehicle is rigid. Orientation of the vehicle with respect to the center of the pipe elbow is effected before it is introduced. Due to practically unavoidable measuring inaccuracies, a lateral offset may result between the vehicle and the orientation or alignment axis per se prior to or during the insertion. So that the vehicle can travel farther unhindered without jamming, there is provided, in accordance with a further feature of the invention, a cross slide member for supporting the multimember vehicle on the manipulator mast arm so that a lateral offset between the vehicle inserted or introduced into the pipe elbow and the mast arm can be equalized, the cross slide member being lockable in the extended readiness position of the vehicular members and the test system carrier for centering and orienting or aligning the multimember vehicle. This equalization is of advantage also if the vehicular member closest to the mast should travel into the curved region. In accordance with an alternate feature of the invention, the vehicular member which is closest to the manipulator mast comprises a telescopic linkage which is either connected to the arm or fastened to a joint flange of the universal joint or cross slide member on the side of the multimember vehicle. It is thereby possible to cover the test area disposed in direction of the pipe axis virtually in all cases; the vehicular member closest to the mast, as mentioned hereinbefore, can also travel into the curved region. To define the extended readiness position, in accordance with an additional feature of the invention, orientation or alignment stops are disposed on the straps and on the vehicular members as well as on the test system carrier, the orientation stops being in flush engagement with one another in the extended readiness position of the vehiclular members and the test system carrier. In principle, electrical, pneumatic or hydraulic drives for the vehicle are possible. However, pneumatic drives are preferably used because possible leakage of the hydraulic fluid is thereby precluded from the start, and, nevertheless, the necessary forces for rugged construction can be supplied. Pneumatic actuators or drives are, therefore, preferably used for driving the support leg-telescopes, for aligning or bending the chain of vehicular members, for axially shifting or displacing the vehicle and for extending or outwardly driving the test arms of the test system carrier, as well as also for operating an ultransonic centering eye mounted on an axial-radial linkage. More specifically in accordance with another feature of the invention, adjustable drive members are provided articulatingly connected to the vehicular members and the test system carrier for converting the vehicular members and the test system carrier between the curved travelling position thereof and the extended readiness position thereof. In accordance with a further feature of the invention, the adjustable drive members are pneumatic power cylinders having compressed air cylinders for operating the vehicular members and the test system carrier in the travelling position thereof, the compressed air cylinders being ventable for effecting a loose coupling of the vehicular members and the test system carrier. In accordance with an added feature of the invention, one of the vehicular members closest to the manipulator mast comprises a hollow telescopic linkage and the other of the vehicular members being also hollow and including a universal shaft drivable from the manipulator mast-side and connected to the test system carrier for rotating the carrier, the universal shaft extending from the mast arm through the cross slide member, the hollow telescopic linkage and said hollow vehicular members, and roller bearing means for rotatably mounting the universal shaft in the vehicular members, individually, and at the test system carrier. In accordance with an additional feature of the invention, adjustable drive members are articulatingly connected to the vehicular members and the test system carrier for converting the vehicular members and the test system carrier between the curved travelling position thereof and the extended readiness position thereof, and an additional drive member for driving the telescopic linkage, the additional drive member being disposed axially parallel to the telescopic linkage and being linked, on the one hand, to the vehicular member closest to the manipulator mast and, on the other hand, to a foot tube of the telescopic linkage. In accordance with yet another feature of the invention, the additional drive member comprises a pneumatic power cylinder. In accordance with yet a further feature of the invention, twoarmed symmetrical roller levers are oriented in travel direction of the multimember vehicle located at the ends of the support legs of the vehicular members and rigidly connected to the support legs so that a respective support leg adjusts itself axially normal to the curvature of the pipe elbow. In accordance with yet an added feature of the invention, the support legs are hollow and are formed as telescopic linkages, and, in the interior of the hollow support legs, a drive for longitudinally adjusting and for pressing the rollers of the roller levers against the inner surface of the pipe elbow in the respective testing position is provided. In accordance with yet an additional feature of the invention, at least three of the support legs are provided for each of the vehicular members in an axially normal plane. In accordance with another feature of the invention, the drives for the hollow support legs are also pneumatic power cylinders linked, on the one hand, to the roller levers and, on the other hand, to a telescopic foot tube. In accordance with a further feature of the invention, axially and radially extensible linkages of an ultrasonic centering eye are mounted on the front side of the test system carrier. In accordance with concomitant features of the invention, the test arm of the test system carrier is formed as a hollow telescopic arm and an adjustable drive therefor, preferably a pneumatic power cylinder, is mounted therein.

Other features which are considered as characteristic for the invention are set forth in the appended claims.

Although the invention is illustrated and described herein as embodied in elbow or bent tube manipulator, especially for ultrasonic testing in nuclear installation, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, in which.

Figure 1A:
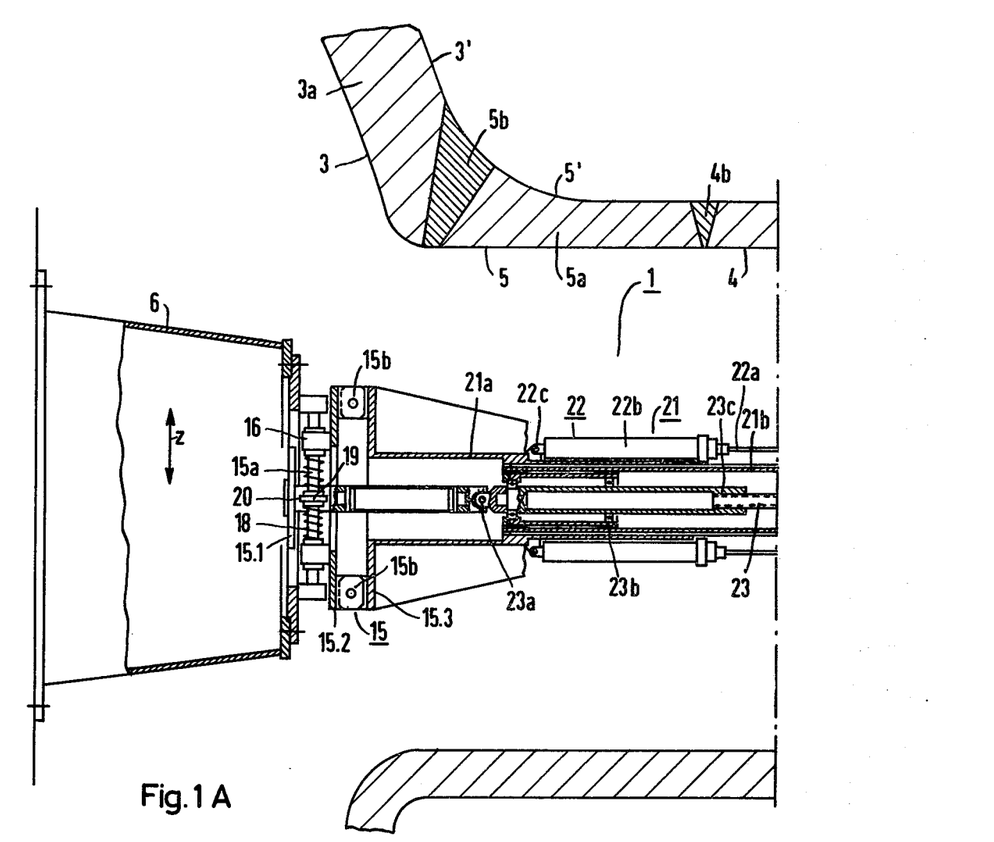
FIGS. 1A and 1B are two contiguous parts of a fragmentary crosssectional view of a manipulator constructed in accordance with the invention having two vehicular members and a test system carrier introduced into a pipe elbow.
Figure 1B:
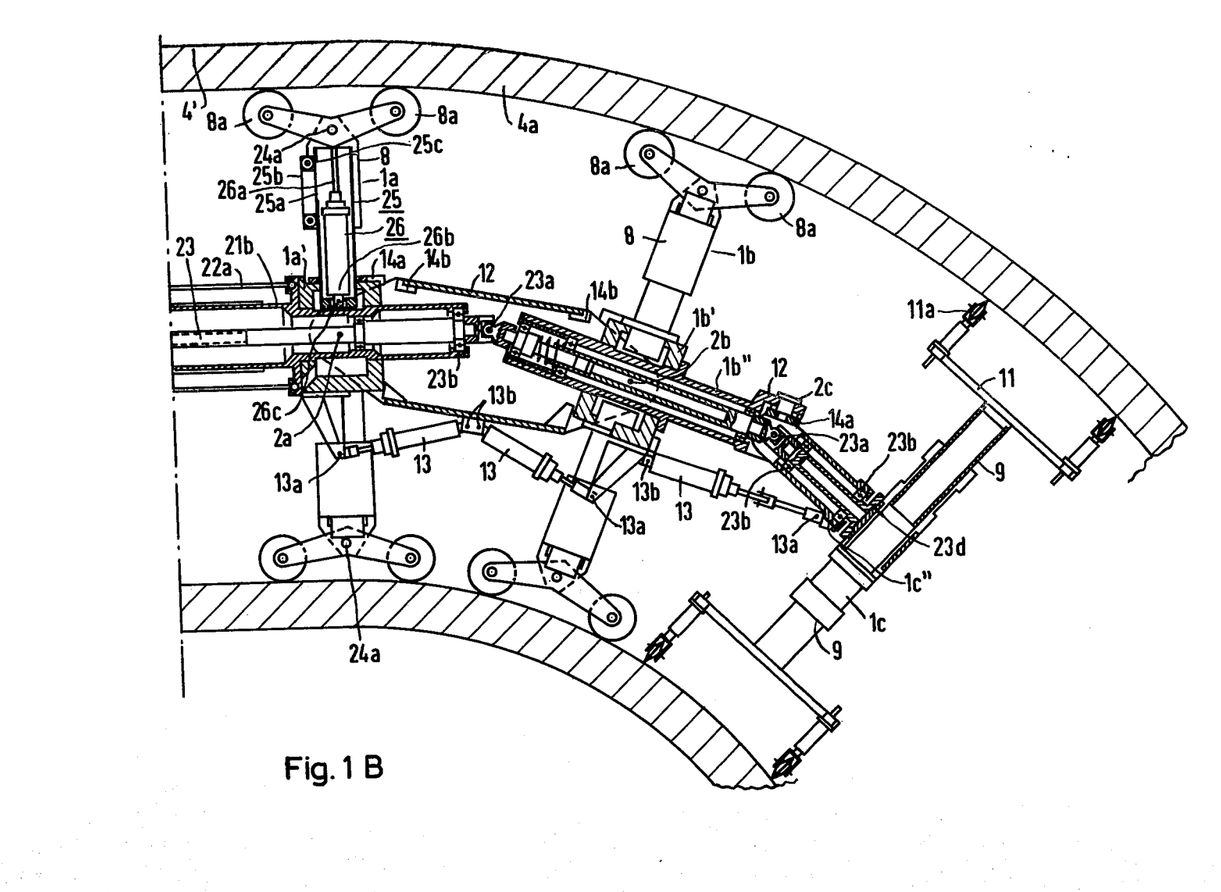
Figure 2:
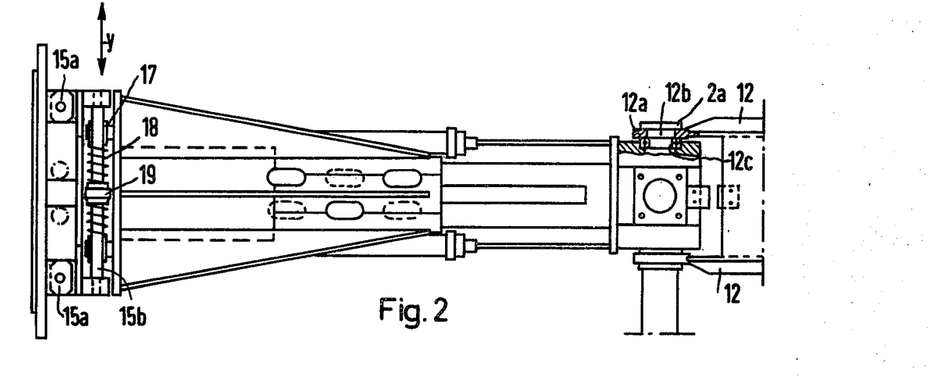
FIG. 2 is a fragmentary view of a composite of FIGS. 1A and 1B rotated 90° about an axis disposed in the plane of the drawing of FIGS. 1A and 1B showing details of an universal joint and a telescope provided in the vehicular member shown at the left-hand side of the composite of FIGS. 1A and 1B.
Figure 3:
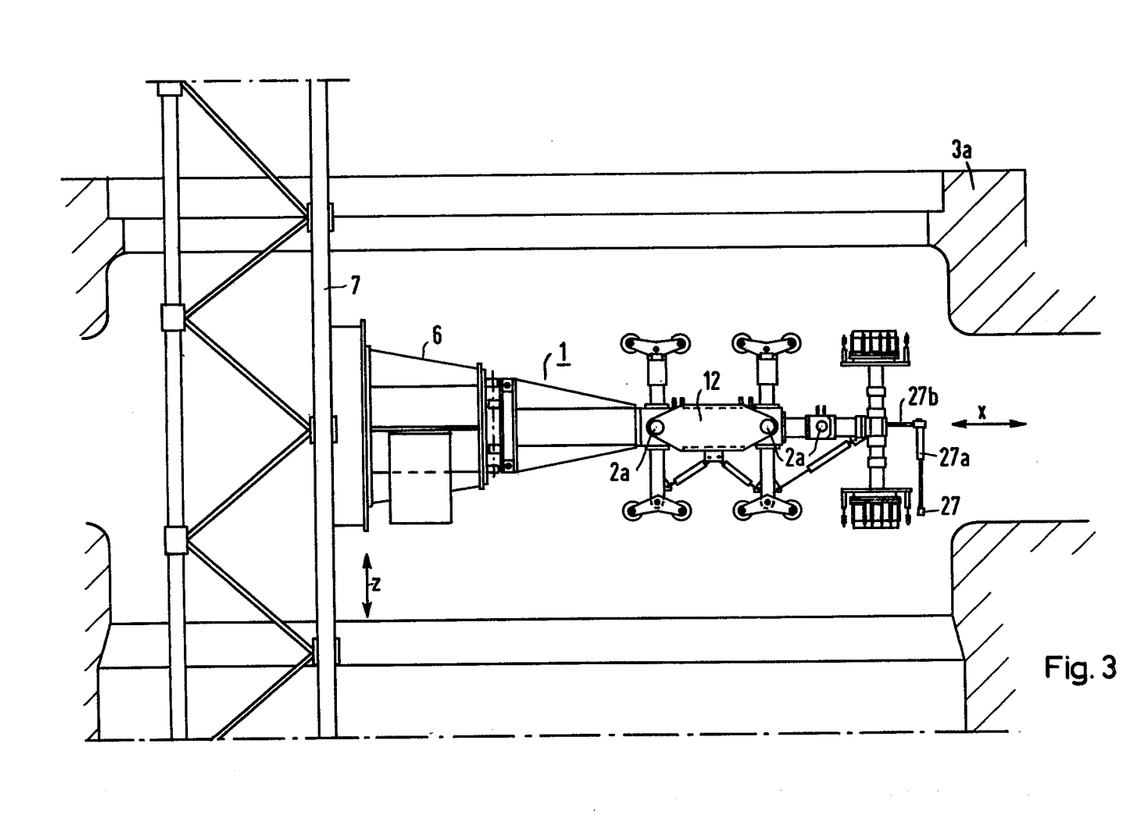
FIG. 3 is an elevational view of the manipulator of FIG. 1, in reduced scale, showing the manipulator in extended ready-position prior to the introduction thereof into a pipe elbow, part of a manipulator mast and an ultrasonic eye being also shown.
Figure 4:
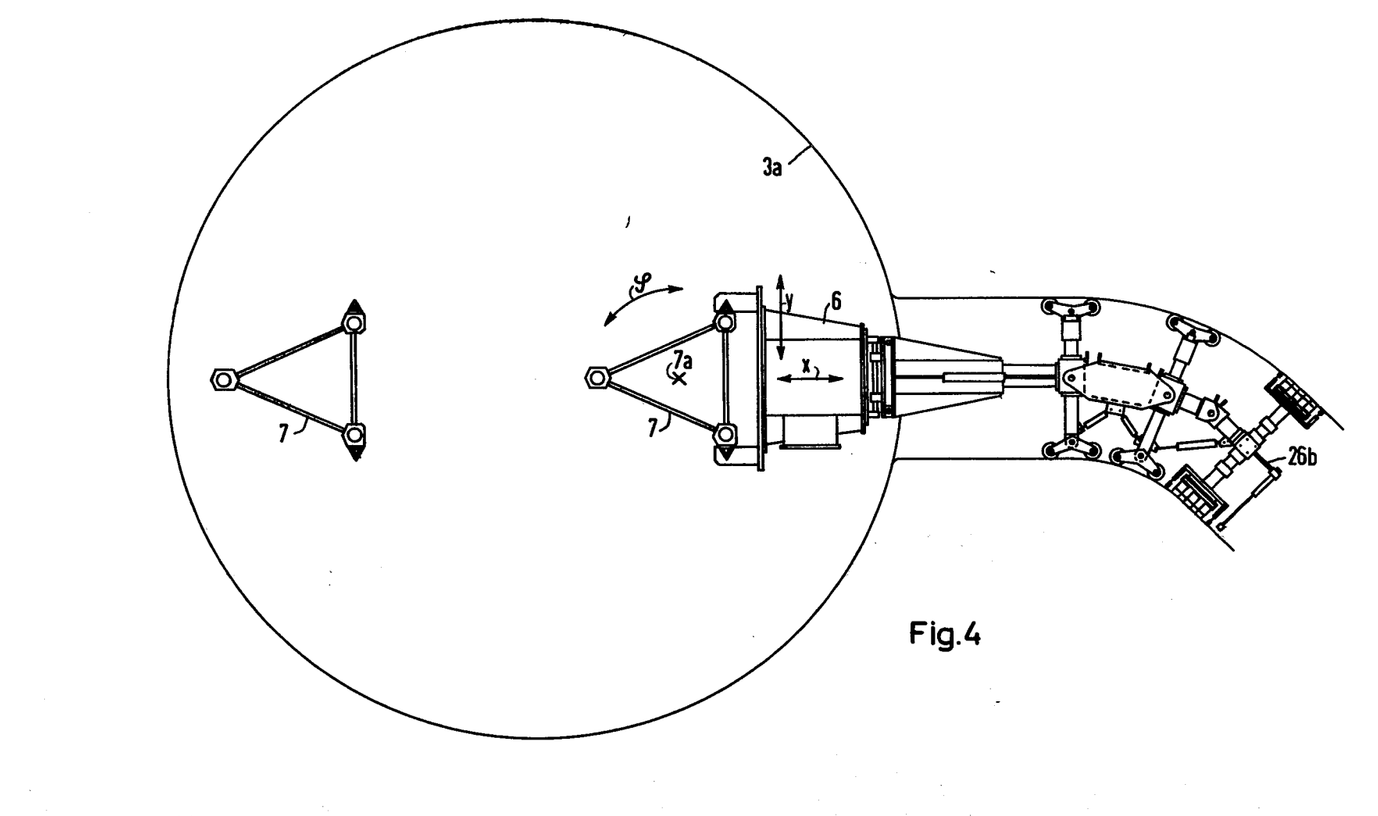
FIG. 4 is a diagrammatic top plan view of FIG. 3 with the manipulator, however, in another position thereof wherein it is inserted into the pipe elbow.
Figure 5:
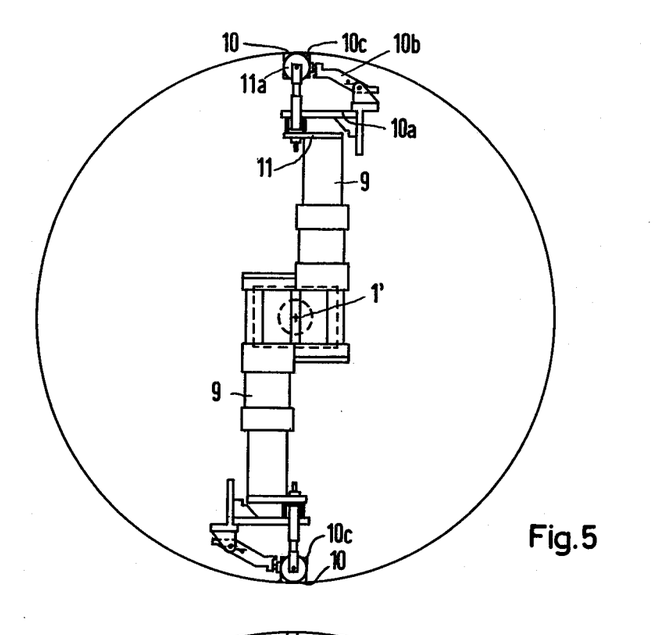
FIG. 5 is a slightly enlarged view of the test system carrier of FIG. 1B having two test arms.
Figure 6:
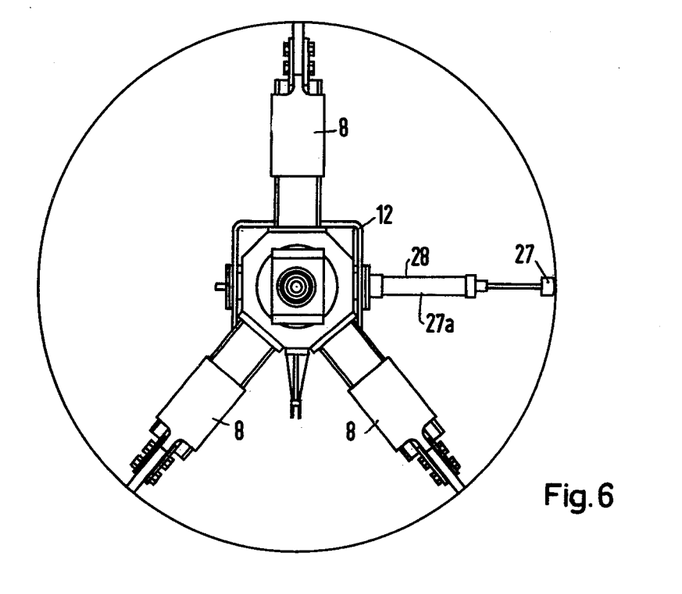
FIG. 6 is a slightly enlarged side view of one of the vehicular members of FIG. 1B showing the three support legs thereof and the ultrasonic eye with the linkage therefor.

Referring now to the drawing and first, particularly to FIG. 1 thereof, there is shown a manipulator generally identified in its entirety. The manipulator 1 includes a first vehicular member 1a, a second vehicular member 1b and a test system carrier member 1c, the members 1a, 1b and 1c being articulatingly interconnected by joints 2a (see FIG. 2), 2b and 2c to form a multimember vehicle. The inner contour 3 of a reactor pressure vessel 3a of an otherwise non-illustrated nuclear reactor installation and the inner contour 4 of a pipe elbow 4a of a curved main coolant line, as well as corresponding outer contours 3' and 4' and an inner and an outer contour 5 and 5', respectively, of a connecting pipe or union for the pressure vessel 3a are shown in FIGS. 1A and 1B. The reactor coolant line is one of several that are disposed with uniform distribution over the peripheral surface of the reactor pressure vessel 3a. An union seam 5b and a pipe connection seam 4b are also shown in FIG. 1A, however, longitudinal seams which are conventionally provided within the pipe elbow are not specifically shown in FIGS. 1A or 1B. The manipulator 1 is supported on an arm 6 of a mast manipulating device 7, a section of which can be seen in FIGS. 3 and 4. Within the opened reactor pressure vessel 3a, the manipulator 1 is adjusted in height in Z-direction (double-headed arrow Z) by the mast manipulating device 7 or the arm 6, respectively, is rotatable about the mast axis 7a (arrow φ in FIG. 4), and adjustable in longitudinal and transverse directions (arrows x and y, respectively, in FIG. 4). The vehicular members 1a, 1b (see FIGS. 1A and 1B) are supportable in a centered position relative to the inner peripheral surface 4 of the pipe 4a by means of extensible and retractable support legs 8, and are capable of traveling in longitudinal direction of the pipe (x-axis) by means of roller members 8a mounted at the ends of the support legs 8. Also the test system carrier 1c at the head of the manipulator 1 is movable in direction of the pipe axis by means of the manipulator 1 and the vehicular members 1a and 1b. The test system carrier 1c has two test arms 9 (see also FIG. 5), to each of which one test system 10, respectively, is fastened, at the outer end, and further, as shown in FIG. 1, a respective support roller arm 11 provided with a support roller 11a. The respective test systems 10 are fastened to the support roller arms 11, respectively, and are formed, respectively, of a mounting plate 10a, rocker arm system 10b and ultrasonic test heads 10c per se, which are fastened, in conventional manner, in gimbals to the rocker arms 10b, for universal movement. The test arms 9 are disposed parallel to one another on chords, and have a point symmetry relative to the central axis 1' of the manipulator 1, so that each of the test systems 10, with the test heads 10c thereof, scans or travels over corresponding test tracks at the inner periphery 4 of the pipe elbow 4a when the test system carrier 1c is rotated. If the test systems 10 with the test heads 10c thereof, are disposed opposite one another in the same test tracks, a rotation of about 180° is sufficient for a complete scan; otherwise, the test system carrier must be rotated 360°, in which case twice the number of test tracks can be scanned, however. In this connection, the test system carrier 1c rolls along with the support rollers 11a thereof in a position normal to the axis, and central to the respective pipe elbows cross section. The vehicular members 1a and 1b and the test system carrier 1c are articulatingly coupled to one another by means of the hereinaforementioned articulating couplings 2a, 2b and 2c, the manipulator, in fact, being provided for scanning pipe lines curved in one plane, so that these articulating couplings accordingly permit curvature only in one plane, while the vehicle is rigid in other planes axial to the pipe. The articulating couplings (note also FIG. 2) are formed of joint or articulating straps 12 with joint or articulating eyes 12a, pins 12b and roller bearings 12c. The articulating joints 2b and 2c are of similar construction, the articulating coupling 2c shown being rotated through an angle of 90° for better understanding. The vehicular members 1a and 1b and the test system carrier 1c are furthermore in engagement with one another through actuating members 13 which are adjustable in length. The latter are formed of pneumatic power cylinder systems the pistons of which are linked at 13a and the cylinders at 13b to the vehicular members 1a and 1b, the test system carrier 1c and the joint or articulating straps 12. The joint or articulating straps 12, and the vehicular members 1a and 1b, as well as the test system carrier 1c, are provided with stops 14a and 14b, which flushly engage one another in the extended readiness position (FIG. 3), so that this position is unequivocally and exactly defined. The manipulator 1 can be brought, for example, from the curved position thereof shown in FIGS. 1A and 1B, into the extended position thereof according to FIG. 3 by actuating the power cylinders 13, the pressure medium lines leading to these power cylinders as well as to other power cylinder systems to be described further hereinafter, being non-illustrated in the interest of simplification and clearer presentation. According to FIG. 3, the manipulator 1 is oriented in the direction x of the axis of the union or connecting pipe and centered with the pipe center, in the extended readiness position thereof, before the manipulator 1 is introduced into the pipe line 5a, 4a, the vehicular members 1a and 1b and the test system carrier 1c being rigidly coupled to one another. In the travel position (FIG. 4 and FIGS. 1A and 1B), however, wherein possibly one vehicular member 1b and at least the test system carrier 1c are located in the curved region of the pipe 5a, 4a, the vehicular members 1a and 1b and the test system carrier 1c are loosely coupled together, so that they adapt themselves to the pipe curvature 5 during the advance or feed in direction of the pipe axis x. For this travel position, the pneumatic power cylinders 13 are depressurized, i.e., are vented. The vehicle 1a, 1b, 1c, i.e., the vehicular member 1a thereof, is supported in such a manner by means of a cross-slide section 15 at the arm 6 of the mast manipulator 7 (note, in particular, FIGS. 1A and 2), that a lateral offset between the introduced vehicle and the arm 6 can be equalized, while the cross-slide section 15 can be locked for centering and orienting the vehicle in the extended readiness position thereof. In particular, the cross-slide section 15 is formed of guide rod pairs 15a, 15b disposed between three flanges 15.1, 15.2 and 15.3, the flange 15.2 being mounted on the guide rods 15a by sleeves 16 so as to be shiftable in z-direction and the flange 15.3 being mounted by sleeves 17 on the guide rods 15b so as to be shiftable in y-direction, coil compression springs 18 being mounted on the guide rods 15a and 15b for restoring the flanges to the null or neutral position thereof. The described guide unit of the cross-slide section is locked by centering pins 19 which engage in corresponding slots 20, when the manipulator is aligned (FIG. 3). The first vehicular member 1a includes a telescopic linkage 21 with a base or foot tube 21a and a sliding tube 21b, the latter being firmly connected to the vehicular member 1a and the base tube 21 being firmly connected to the flange 15.3 of the cross-slide section 15. A pneumatic power cylinder system serves again as the positioning drive 22 for the telescopic tube 21, the piston rod 22a thereof being linked or articulatingly connected to the base portion 1a' of the vehicular member 1a, and the cylinder thereof being linked or articulatingly connected to the base or foot tube 21a of the telescopic tube 21 at 22c. Two diametrically opposed drive systems 22 are used (note FIGS. 1a and 2). For the rotary drive of the test systm carrier 1c, the latter could be associated directly with a motor and a transmission or reduction gear. In the illustrated embodiment, the especially rugged construction of a universal shaft 23 is selected, having universal joints 23a and roller bearings 23b therefor. The universal shaft 23 extends from the arm 6 through the cross-slide section 15, the hollow telescopic linkage 21 and the hollow vehicular members 1a and 1b, i.e., through the hollow base portions 1a' and 1b' thereof, all the way to the test system carrier 1c. It is rotatably drivable by means of a drive motor with transmission (not otherwise shown in detail), which is disposed within the arm 6. The roller bearings 23b are disposed within the telescopic tube 21b and within the hollow tubes 1b", 1c" associated with the vehicular member 1b and the test system carrier 1c. The universal shaft 23 is adjustable in length by means of the screw connection 23c. The test system carrier 1c with the test arms 9 thereof, is flanged to the free end 23d of the universal shaft 23, the test arms 9 are also constructed as hollow telescopic arms, containing in the interior thereof a positioning drive, preferably a respective pneumatic power cylinder (not further illustrated specifically). Due to this drive, the test arms 9 can be extended and retracted approximately radially and, thus, the support rollers 11a and the test heads 10 brought into position. The test heads 10 have been omitted in FIG. 1B and are shown only in FIG. 5. These power cylinder systems, which are not further illustrated with regard to the test system carrier 1c, are constructed somewhat as shown in further detail in the vehicular member 1a (FIG. 1B). The support legs 8 of the vehicular member 1a and, correspondingly, also of the vehicular member 1b are provided at the ends thereof with double-armed symmetrical roller levers 24 which are oriented in the travel direction and are rigidly connected to the support legs 8 at 24a in such a manner that the respective support leg 8 adjusts itself so that it is normal to the axis of the pipe elbow 4a, 5a. The rigid coupling 24a is formed by a tightened screw connection. Like the hereinaforedescribed test arms 9, the support legs 8 are hollow and constructed as a telescopic linkage 25, with a base or foot tube 25a and a sliding tube 25b, the latter being slidable, accurately guided, along the outer periphery of the base or foot tube 25a by means of rollers 25c. A pneumatic power drive 26, piston rods 26a and a cylinder 26b are provided, the latter being linked at 26c to the base or foot tube 25a and the piston rods 26a to the threaded bolt 24a which is connected to the sliding tube 25b. In the respective measuring position of the manipulator 1, the rollers 8a are forced firmly against the inner wall surface of the pipe 4a, 5a, by actuating the pneumatic drives 26, and the manipulator 1 is thereby unequivocally tightened and fixed. As shown in FIG. 6, three support legs 8 disposed in a plane normal to the axis, are provided for each vehicular member 1a and 1b. This produced a defined three-point contact. FIG. 6 is a view in direction toward the free, head-side end of the manipulator 1, where the radial arm 27a of an ultrasonic centering eye 27 is visible. FIGS. 3 and 4 show more clearly the axial linkage 27b, which extends out of the test system carrier 1c through an axial hole, not shown in FIG. 1B, the radial arm 27a of the ultrasonic centering eye 27 containing a pneumatic power cylinder 28 (FIG. 6). With this ultrasonic eye 27, the manipulator 1 (note FIG. 3) can be inserted, in the extended readiness position thereof, a short distance into the pipeline 4a, 5a; then, by rotating the arm 27a, the exact centered position of the manipulator 1, i.e., the orientation thereof along the x-axis, can be established, additional intermediate checks of the centered position of the manipulator 1 being possible also in the test position according to FIGS. 1 and 4. Inasmuch as it is not already evident from the foregoing, the operation of the manipulator 1 is as follows: After the manipulator 1 has been introduced into the opened reactor pressure vessel (which is usually filled with water for the purpose of in-service inspection tests), the manipulator 1 is brought into the extended readiness position thereof, as shown in FIG. 3 and centered by the ultrasonic eye 27 on the pipe center. During this operation, the cross-slide member 15 is blocked or locked. Then, the manipulator 1 is insertable slowly by means of the telescope 21 into the pipe 4a, 5a, while the cross-slide member 15 is unblocked or unlocked and while also the pneumatic drives 13, which were subjected to pressure in the position thereof, according to FIG. 3, are then depressurized or vented, so that the manipulator 1, with the vehicular member 1b thereof, is able to follow the curvatures of the pipe. The test system carrier 1c remains retracted then and therefore does not yet touch the pipe walls with the rollers 11a and the test heads 10 thereof. If this first test position is reached, then the support legs 8 are locked or blocked by actuation of the pneumatic drives 26, and the test system carrier with the rollers 11a and the test heads 10 thereof are brought into the test position by means of the pneumatic drive thereof. The test system carrier 1c can then slowly scan the test tracks thereof by slow rotation of the universal shaft 23 along the test path. For scanning further test tracks, the test system carrier 1c is again disengaged with respect to the surface of the pipe wall, the rollers 8a are again released or relieved of stress by actuation of the pneumatic drives 26 and, by actuating the telescope 21 with the aid of the power cylinders 22, the manipulator 1 can be driven into and again out of the next axial test position. It should further be noted that, in the left-hand side of FIG. 4, a preliminary position of the mast manipulator 7 is shown.

There are claimed:

1. Manipulator assembly for testing the material of a pipe elbow from the inside thereof, the pipe elbow being secured to a pipe union extending from a pressure vessel openable for receiving therein a vertically extending manipulator mast having an arm carrying a manipulator, the manipulator being movable by the arm in vertical direction, rotatably about the axis of the mast and in direction of the longitudinal axis of the arm and transversely thereto, the manipulator comprising a multimember vehicle drivable in direction of the pipe-union and pipe-elbow axis, the members of said vehicle being articulatingly connected to one another and having extensible and retractable support legs for supporting the respective vehicular members centered relative to the inner periphery of the pipe elbow, said support legs having roller members at the end thereof for transporting the vehicular members in axial direction of the pipe union and the pipe elbow, the vehicular member located at the head of said multimember vehicle being a test system carrier and being drivable with said vehicle in axial direction of the pipe union and the pipe elbow, said test system carrier having a test system fastened to at least one test arm and mounted so as to be rotatable along predetermined test tracks in circumferential direction of the pipe elbow, drivable radially inwardly and outwardly with said test arm and centerable on the respective center of the pipe elbow, said vehiculer members and said test system carrier being mutually engaged by articulating couplings and longitudinally adjustable drive members so that, in an extended readiness position thereof wherein the manipulator is disposed in front of the pipe union, said vehicular members and said test system carrier are oriented in axial direction of the pipe union, are centered on the pipe-union center and are rigidly coupled to one another, whereas in a travelling position thereof wherein at least said test system of the manipulator is located within the pipe elbow, said vehicular members and said test system carrier are loosely coupled to one another so that they adapt themselves to the curvature of the pipe elbow as they travel in axial direction thereof.

2. Manipulator assembly according to claim 1 including a cross slide member for supporting said multimember vehicle on the manipulator mast arm so that a lateral offset between said vehicle introduced into the pipe elbow and the mast arm is equalizable, said cross slide member being lockable in said extended readiness position of said vehicular members and said test system carrier for centering and orienting said multimember vehicle.

3. Manipulator assembly according to claim 1 wherein one of said vehicular members closest to the manipulator mast comprises a telescopic linkage connected to said arm.

4. Manipulator assembly according to claim 2 wherein one of said vehicular members closest to the manipulator mast comprises a telescopic linkage, and wherein said cross slide member has a flange to which said telescopic linkage is fastened.

5. Manipulator assembly according to claim 1 including straps articulatingly connecting said vehicular members and said test system carrier so that said multimember vehicle is capable of effecting in a given plane a deflection corresponding to the curvature of the pipe elbow whereas in other planes axial to the pipe elbow said multimember vehicle is rigid.

6. Manipulator assembly according to claim 5 including orientation stops disposed on said straps and on said vehicular members as well as on said test system carrier, said orientation stops being in flush engagement with one another in said extended readiness position of said vehicular members and said test system carrier.

7. Manipulator assembly according to claim 6 including adjustable drive members articulatingly connected to said vehicular members and said test system carrier for converting said vehicular members and said test system carrier between said curved traveling position thereof and said extended readiness position thereof.

8. Manipulator assembly according to claim 7 wherein said adjustable drive members are pneumatic power cylinders having compressed air cylinders for operating said vehicular members and said test system carrier in said travelling position thereof, said compresed air cylinders being ventable for effecting a loose coupling of said vehicular members and said test system carrier.

9. Manipulator assembly according to claim 2 wherein one of said vehicular members closest to the manipulator mast comprises a hollow telescopic linkage and the other of said vehicular members being also hollow, and including a universal shaft drivable from the manipulator mast-side and connected to said test system carrier for rotating said carrier, said universal shaft extending from the mast arm through said cross slide member, said hollow telescopic linkage and said hollow vehicular members, and roller bearing means for rotatably mounting said universal shaft in said vehicular members, individually, and at said test system carrier.

10. Manipulator assembly according to claim 4 including adjustable drive members articulatingly connected to said vehicular members and said test system carrier for converting said vehicular members and said test system carrier between said curved travelling position thereof and said extended readiness position thereof, and an additional drive member for driving said telescopic linkage, said additional drive member being disposed axially parallel to said telescopic linkage and being linked, on one hand, to the vehicular member closest to the manipulator mast and, on the other hand, to a foot tube of said telescopic linkage.

11. Manipulator assembly according to claim 10 wherein said additional drive member comprises a pneumatic power cylinder.

12. Manipulator assembly according to claim 1 including two-armed symmetrical roller levers oriented in travel direction of said multimember vehicle located at the ends of said support legs of said vehicular members and rigidly connected to said support legs so that a respective support leg adjusts itself axially normal to the curvature of the pipe elbow.

13. Manipulator assembly according to claim 12 wherein said support legs are hollow and are formed as telescopic linkages, and including in the interior of said hollow support legs a drive for longitudinally adjusting and for pressing the rollers of said roller levers against the inner surface of said pipe elbow in the respective testing position.

14. Manipulator assembly according to claim 12 wherein at least three of said support legs are provided for each of said vehicular members in an axially normal plane.

15. Manipulator assembly according to claim 13 wherein said drives for said hollow support legs are also pneumatic power cylinders linked, on the one hand, to said roller levers and, on the other hand, to a telescopic foot tube.

16. Manipulator assembly according to claim 1 including axially and radially extensible linkages of an ultrasonic centering eye mounted on the front side of said test system carrier.

17. Manipulator assembly according to claim 1 wherein said test arm of said test system carrier is formed as a hollow telescopic arm, and including an adjustable drive therefor mounted therein.

18. Manipulator assembly according to claim 17 wherein said adjustable drive for said telescopic arm of said test system carrier is a respective pneumatic power cylinder.

* * * * *